US00PP35364P2

(12) United States Plant Patent
Olesen

(10) Patent No.: US PP35,364 P2
(45) Date of Patent: Sep. 5, 2023

(54) GROUND COVER ROSE PLANT NAMED 'POULTC027'

(50) Latin Name: *Rosa hybrida*
Varietal Denomination: Poultc027

(71) Applicant: Mogens Nyegaard Olesen, Fredensborg (DK)

(72) Inventor: Mogens Nyegaard Olesen, Fredensborg (DK)

(73) Assignee: POULSEN ROSER NS, Fredensborg (DK)

( * ) Notice: Subject to any disclaimer, the term of this patent is extended or adjusted under 35 U.S.C. 154(b) by 0 days.

(21) Appl. No.: 17/803,628

(22) Filed: Sep. 13, 2022

(30) Foreign Application Priority Data

Sep. 24, 2021 (QZ) ..... PBR 2021/2349

(51) Int. Cl.
*A01H 5/02* (2018.01)
*A01H 6/74* (2018.01)

(52) U.S. Cl.
USPC ..... Plt./101

(58) Field of Classification Search
USPC ..... Plt./101
See application file for complete search history.

*Primary Examiner* — Susan McCormick Ewoldt

(57) ABSTRACT

A new garden rose plant of the Ground Cover class which has abundant, orange flowers and attractive foliage. This new and distinct variety has shown to be uniform and stable in the resulting generations from asexual propagation.

3 Drawing Sheets

Botanical designation: *Rosa hybrida.*

Variety denomination: 'Poultc027'.

This application claims priority to Plant Breeder's Rights Application Number 2021/2349, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed seedling, and the male pollen parent, also an unnamed seedling. Both of the parent varieties are non-patented.

The two parents were crossed during the summer of 2011 and the resulting seeds were planted in a controlled environment in Fredensborg, Denmark. The new variety, named 'Poultc027', originated as a single seedling from the stated cross.

The new variety may be distinguished from its male pollen parent and female seed parent primarily by the following characteristics. The male pollen parent plant has a different growth habit, measuring 30 cm in height and 30 cm wide. The new variety is more compact and spreading, with a growth height of 25 cm width of 48 cm. The female seed parent plant has red flowers while the new variety has orange flowers.

The objective of the hybridization of this rose variety was to create a new and distinct variety with unique qualities, such as:

1. Uniform and abundant orange flowers;
2. Vigorous, but compact growth when propagated on its own roots;
3. Exceptional disease resistance.

This combination of qualities is not present in previously available commercial cultivars of this type, known to the inventor, and distinguish 'Poultc027' from all other varieties of which we are aware.

As part of the rose development program, Mogens N. Olesen germinated the seeds from the aforementioned hybridization during winter of 2011 and conducted evaluations on the resulting seedlings in a controlled environment in Fredensborg, Denmark. 'Poultc027' was selected in the spring of 2012 by the inventor as a single plant from the progeny of the aforementioned hybridization.

Asexual reproduction of 'Poultc027' by rooted cuttings was first done by Mogens N. Olesen in the nursery in Fredensborg, Denmark in July, 2012. This initial and other subsequent asexual propagations conducted in controlled environments have demonstrated that the characteristics of 'Poultc027' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poultc027'.

Specifically illustrated in FIG. 1 of the drawings are Open flowers viewed from above and the side, flower buds at stages of opening, flower petals detached revealing the colour patterns on the upper and lower surface, sepals detached revealing receptacle.

Figure 1:
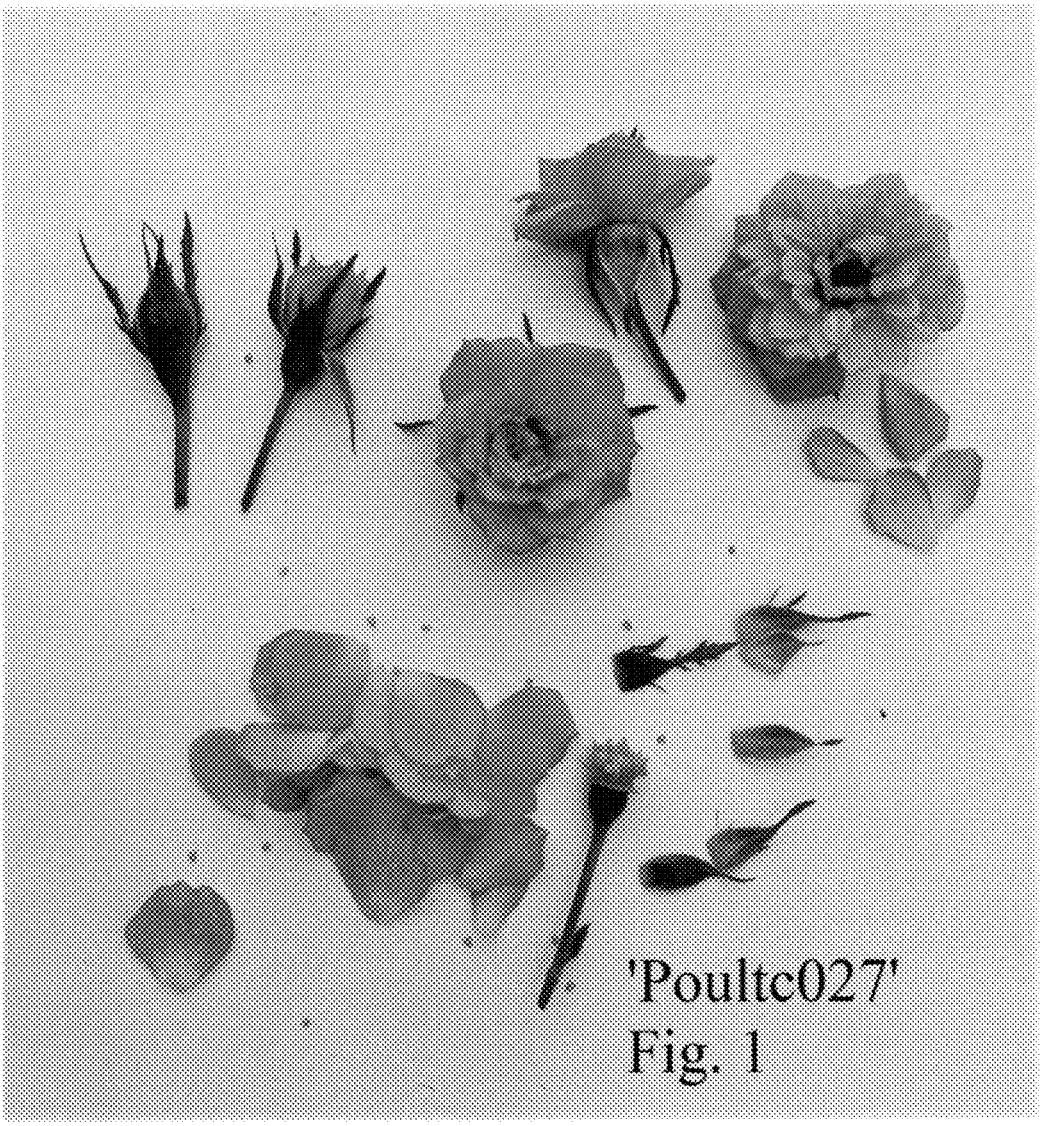
Figure 2:
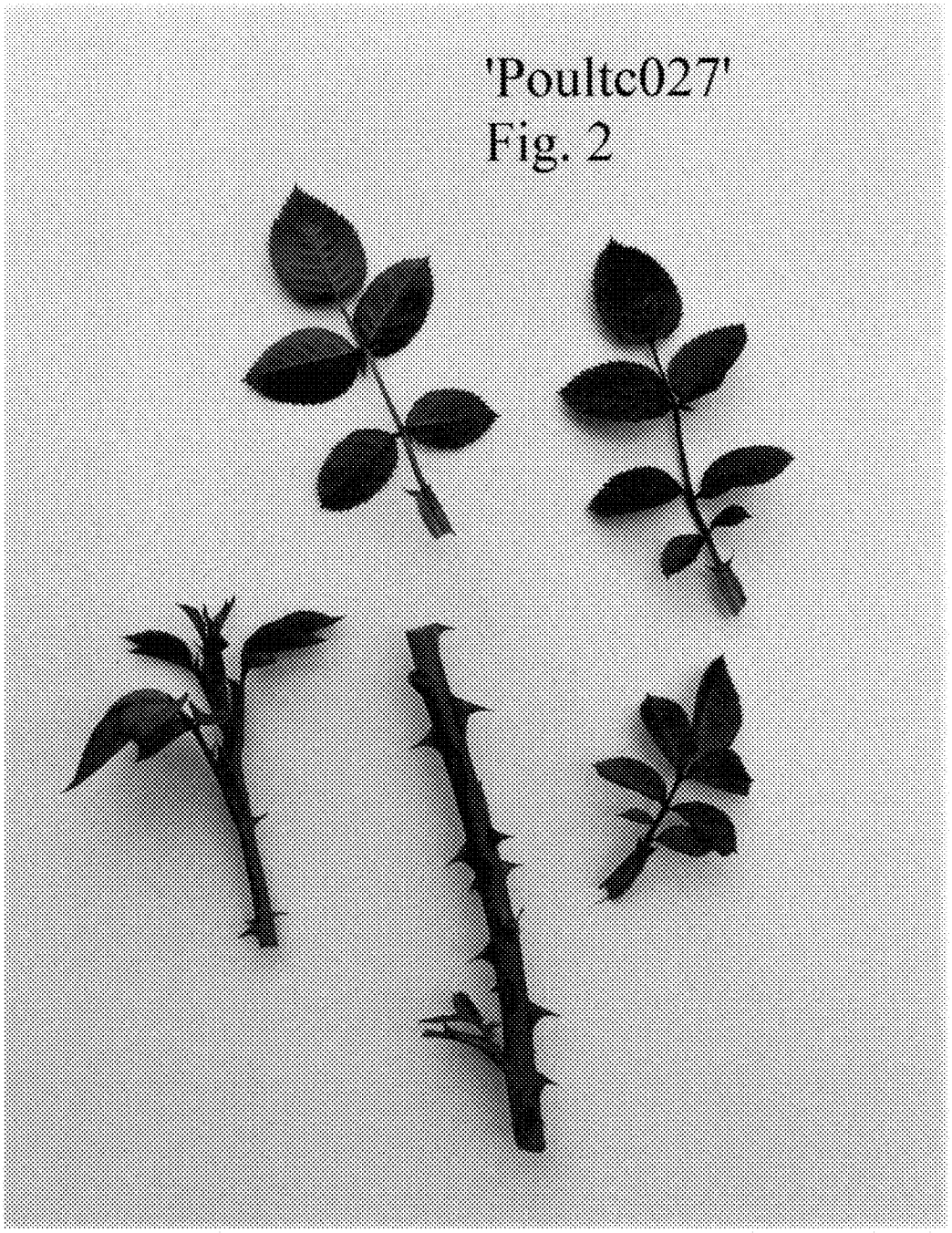

Specifically illustrated in FIG. 2 of the drawings are juvenile bare stem, mature bare stem showing prickles, juvenile and mature leaves.

Figure 3:
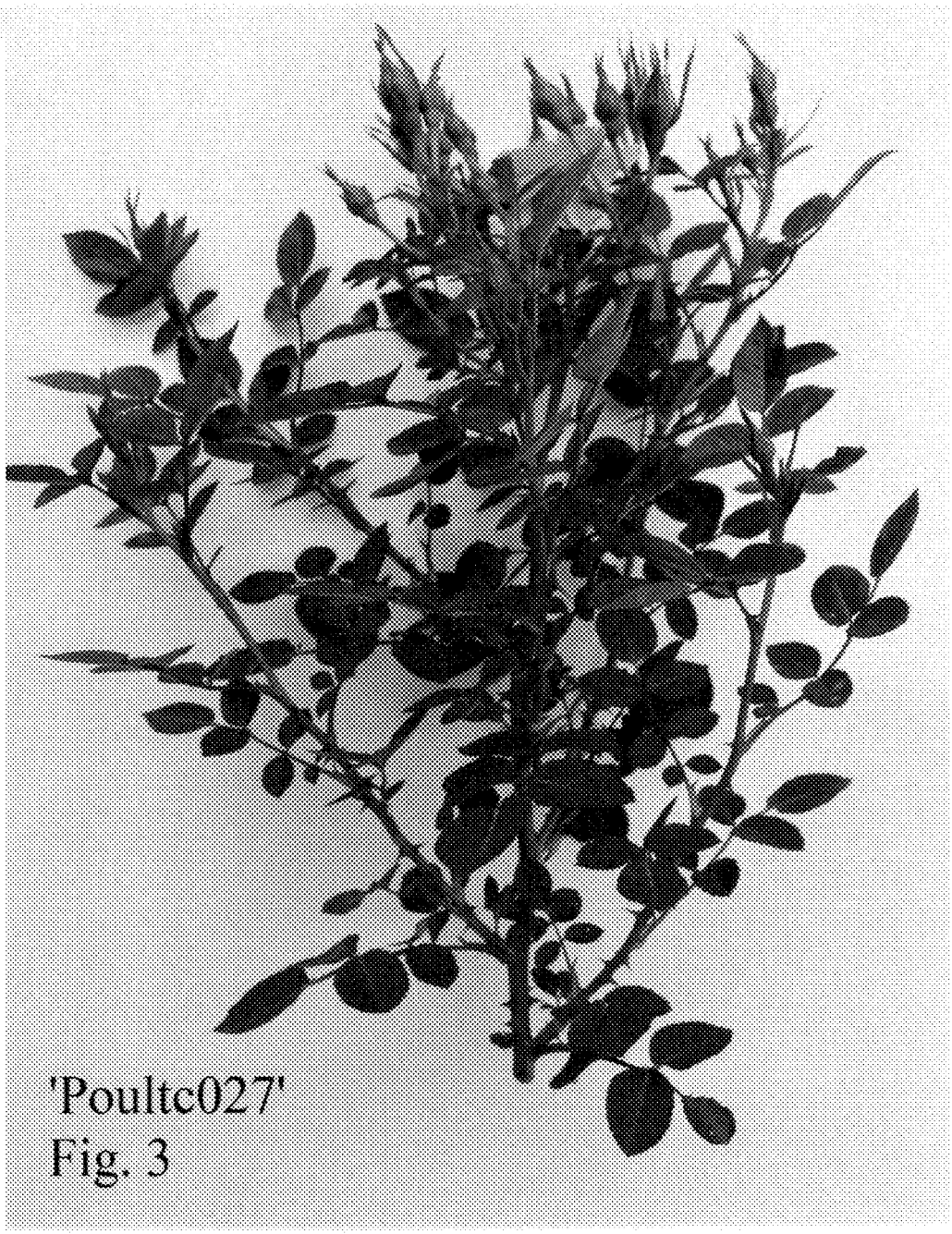

FIG. 3 shows a cluster of flower buds on the branch. Plants shown are 2 years of age.

DETAILED DESCRIPTION OF THE VARIETY

The following is a description of 'Poultc027', as observed in its growth in an outdoor nursery in Odense Denmark.

Observed plants are 15 months of age, and were grown on their own roots in 24 cm pots. Color references are made using The Royal Horticultural Society (London, England) Colour Chart, 2001, except where common terms of color are used.

For a comparison, several physical characteristics of the rose variety 'Poultc021', U.S. Plant Pat. No. 27,574 are compared to 'Poultc027'. The comparison variety has 20 flower petals, while the new plant has 60 flower petals. The comparison has a general flower tonality of Orange-Red Group N30B. The new plant has a general flower tonality of Orange-Red Group N30C. While the claimed plant exhibits flower buds borne in clusters of about 7 to 15 flower buds per stem, the comparison variety exhibits flower buds borne in clusters of 3 to 7 flower buds per stem.

FLOWER AND FLOWER BUD

Blooming habit: Continuous.

Flower bud:

*Size*.—Upon opening, 27 mm in length from base of receptacle to end of bud. Bud diameter is 12 mm.

*Bud form*.—Ovoid.

*Bud color*.—As sepals divide petals are Orange-Red Group 33A.

*Sepal inner surface*.—Color: Yellow-Green Group 146D. Surface: Lightly pubescent.

*Sepal outer surface*.—Color: Yellow-Green Group 144A with intonations of Greyed-Orange Group 166A. Texture: Smooth.

*Sepal shape*.—Apex: Cirrhose. Base: Flat at union with receptacle.

*Sepal margin*.—Margins have strong foliaceous appendages on three of the five sepals.

*Sepal size*.—About 25 mm long, 8 mm wide.

*Receptacle*.—Texture: Smooth. Size: 9 mm in height, 6 mm wide. Color: Yellow-Green Group 144A with intonations of Greyed-Purple Group 183A. Shape: Globose and funnel shape.

*Pedicel*.—Surface: Smooth. Length: 28 mm. Diameter: 2 mm on average. Color: Yellow-Green Group 144A. Strength: Strong.

*Peduncle*.—Length: About 10 to 40 cm. Diameter: About 2 to 3 mm. Color: Yellow-Green Group 145A. Texture: Smooth.

Flower bud development: Flower buds are borne in clusters of about 7 to 15 flower buds per stem. Development as a panicle.

Flower bloom:

*Fragrance*.—Light floral scent.

*Duration*.—The blooms have a duration on the plant of approximately 13 days. Petals fall cleanly away from plant after flowers have fully matured.

*Size*.—Flower diameter is 40 to 45 mm when open. Flower depth is 12 mm.

*Flower shape*.—Rosette double flower with many slightly overlapping petals of different sizes.

*Shape of flower, side view*.—The upper portion is convex, the lower portion is flat concave.

Petalage: Under normal conditions, flowers have about 60 petals.

General tonality of flower: Open flowers are Orange-Red Group N30C. Orange-Red Group 33C after 7 to 10 days.

Petal color:

*Upon opening, outer petals*.—Upper surface: Basal zone, Yellow Group 13A, middle zone and marginal zone Orange Group 28A. Other intonations at the marginal zone Red Group 41B. Lower surface: Basal Yellow Group 4A. Middle zone, Orange-Red Group 32B. Marginal zone Red Group 52A.

*Upon opening, inner petals*.—Upper surface: Orange Group 28A. Lower surface: Orange-Red Group 32B.

*After opening, outer petals*.—Upper surface: Basal zone Yellow Group 12A. Middle zone Orange Group 28A. Marginal zone Red Group 47C. Lower surface: Yellow-Orange Group 12C at basal zone. Middle and marginal zone Red Group 39B.

*After opening, inner petals*.—Upper surface: Basal zone Yellow Group 12A. Middle zone Orange Group 28A. Lower surface: Yellow-Orange Group 12C at basal zone. Middle and marginal zone Red Group 39B.

Petals:

*Petal reflex*.—None.

*Margin*.—Entire, not uniform. Single point at the apex. Moderate undulations.

*Shape*.—Broad and elliptic. Apex shape: Rounded. Base shape: Acute.

*Size*.—21 mm (l)×20 mm (w).

*Texture*.—Smooth.

*Thickness*.—Average.

Petaloids:

*Size*.—11 mm (l) by 4 mm (w).

*Quantity*.—About 20.

*Shape*.—Elliptical with an acute base and rounded apex.

*Color*.—Central bar Yellow Group 12B. Orange Group N25A underneath, Orange Group N25A at lower surface.

Reproductive flower parts:

*Pollen*.—None observed.

*Anthers*.—Size: 2 mm in length. Color: Yellow Group 13A. Quantity: 58 on average.

*Filaments*.—Color: Yellow Group 13A with other intonations of Greyed-Orange Group N163A. Length: 4 mm.

*Pistils*.—Length: 3 mm. Quantity: 20 on average.

*Stigmas*.—Color: Greyed-Yellow Group 160C.

*Styles*.—Color: Red-Purple Group 58A.

*Location of stigmas*.—Inferior in location relative to the length of the filaments and the height of the anthers.

*Hips*.—None Observed.

PLANT

Plant growth: Compact, somewhat spreading, and well branched. Plants are about 25 cm in height, and 48 cm wide.

Stems:

*Color of juvenile growth*.—Yellow-Green Group 144B.

*Color of mature growth*.—Yellow-Green Group 144A.

*Length*.—Canes are about 15 cm from the base of the plant to the flowering portion.

*Diameter*.—About 5 mm.

*Internodes*.—On mature canes about 25 mm between nodes.

*Surface texture*.—Young wood: Smooth. Older wood: Smooth.

Long prickles:

*Incidence*.—About 13 prickles per 10 cm of stem.

*Size*.—Average length of prickles on mature stems is 7 mm.

*Shape*.—Upper portion is linear. Lower portion is concave.

*Color*.—Juvenile prickles: Greyed-Red Group 182B. Mature prickles: Greyed-Purple Group 183B.

Plant foliage:

*Compound leaf*.—90 mm (l)×56 (w).

*Quantity*.—3 leaves per 10 cm of stem on average.

*Leaf bearing angle to the stem*.—45 degrees.

*Color of juvenile foliage*.—Upper side: Yellow-Green Group 146A with intonations of Greyed-Orange Group 166A. Lower side: Yellow-Green Group 144B.

*Color of mature foliage*.—Upper side: Yellow-Green Group 147A. Lower side: Yellow-Green Group 147B.

Plant leaves and leaflets:

*Stipules*.—Size: 18 mm long, 3 mm wide. Quantity: 2 per compound leaf. Shape: Linear, slightly broad based with outward extending apices. Margins: Finely serrated. Color:

*Petiole*.—Length: 20 mm. Diameter: 2 mm. Upper surface color: Yellow-Green Group 144A with intonations of Greyed-Purple Group 183B. Lower surface color: Yellow-Green Group 144A.

*Rachis*.—Length: About 35 mm. Upper surface color: Yellow-Green Group 144A with intonations of Greyed-Purple Group 183A. Lower surface color: Yellow-Green Group 144A.

*Leaflet*.—Quantity: Normally 5 to 7 leaflets. Margins: Serrated. Size: Terminal leaflets are about 31 mm long, 25 mm wide. Shape: Generally elliptical. Base: Rounded. Apex: Acute. Texture: Smooth. Thickness: Average. Arrangement: Odd pinnate. Venation: Reticulate. Glossiness: Very glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poultc027' substantially as described and illustrated herein.

* * * * *

'Poultc027'

'Poultc027'

'Poultc027'